United States Patent [19]

Andersson

[11] Patent Number: 5,052,928
[45] Date of Patent: Oct. 1, 1991

[54] METHOD AND ARRANGEMENT FOR PRODUCING A BRIDGE FOR ANCHORAGE ELEMENTS IN DENTINE

[75] Inventor: Matts Andersson, Fåker, Sweden

[73] Assignee: Nobelpharma AB, Gothenburg, Sweden

[21] Appl. No.: 359,664

[22] PCT Filed: Dec. 2, 1987

[86] PCT No.: PCT/SE87/00574
§ 371 Date: May 16, 1989
§ 102(e) Date: May 16, 1989

[87] PCT Pub. No.: WO88/04158
PCT Pub. Date: Jun. 16, 1988

[30] Foreign Application Priority Data

Dec. 9, 1986 [SE] Sweden .............................. 8605272

[51] Int. Cl.[5] ........................................... A61C 13/225
[52] U.S. Cl. .................................. 433/172; 433/213; 433/229
[58] Field of Search ............... 433/25, 49, 196, 200.1, 433/190, 167, 172, 173, 229, 215, 201.1, 213

[56] References Cited

U.S. PATENT DOCUMENTS

| | | | |
|---|---|---|---|
| 3,068,572 | 12/1962 | Gobby | .................. 433/49 |
| 4,324,546 | 4/1982 | Heitlinger et al. | .................. 433/25 |
| 4,708,654 | 11/1987 | Branemark . | |
| 4,767,328 | 8/1988 | Branemark . | |

FOREIGN PATENT DOCUMENTS

WO8600217 1/1986 PCT Int'l Appl. .
WO8600218 1/1986 PCT Int'l Appl. .
WO8801489 3/1988 PCT Int'l Appl. .
448600 9/1987 Sweden .

Primary Examiner—Cary E. Stone
Attorney, Agent, or Firm—Pollock, Vande Sande & Priddy

[57] ABSTRACT

A bridge for an artificial dental structure is made of titanium. The bridge is constructed from modular elements which are adapted one to the other and are treated for joining together, for example by means of laser welding. In a first treatment unit one or more first treatment stages are performed for the construction of the bridge. Identification data introduced or utilized in this or these stages relating to the individual different heights of the anchorage elements above the dentine and their different relative inclinations, and the positions and directions of the modular elements in relation to one another and to the anchorage elements are obtained and stored. In a subsequent processing stage which is executed by a processing unit the latter is controlled depending on the extracted and stored information, so that any bridge elements present in the bridge between the attachment components of the bridge in the anchorage elements are assured a connection via the contact surfaces and directions and dimensions between the attachment components such that the bridge elements are essentially in line with the direction of the dentine in the sense of its height and width, at the same time with the necessary strength and location within the dental structure.

16 Claims, 2 Drawing Sheets

METHOD AND ARRANGEMENT FOR PRODUCING A BRIDGE FOR ANCHORAGE ELEMENTS IN DENTINE

The present invention relates to a method for producing by mechanical means a bridge made of titanium for anchorage elements implanted in the dentine of a tooth. The aforementioned bridge constitutes the framework for an artificial dental structure, and the dental structure is capable of being attached to the anchorage elements via the bridge. The bridge is of the kind which is built up of modular elements which are treated for the purpose of adapting them one to the other and of being joined together. The invention also relates to an arrangement for the execution of the aforementioned method.

The implantation of titanium pins in the jaw and the anchorage of a bridge structure to these pins has already been disclosed. The bridge structure in this case consists of a framework made of an appropriate material and an artificial dental structure built up on the frame, which dental structure is secured to the pins with screws, preferably made of titanium.

This kind of framework is associated with the need to be able to achieve rational production without being obliged to depart from the requirement for an accurate fit on the pins. The degree of lateral accuracy is high (e.g. $10^{-2}$ mm). Furthermore the requirement in respect of the strength of the bridge is high, a at the same time the bridge framework must be capable of being accommodated within the dimensions of the artificial dental structure. The requirement imposed on the artificial dental structure is that it must correspond to the natural situation which it is to replace.

The above problem is accentuated by the fact that the bridge structure exhibits a high degree of individuality, and the implants can impart different inclinations and heights to the attachment points for the bridge structure. In spite of this there is a wish for an accelerated manufacturing operation and arrangements for the manufacture of a bridge structure of this kind.

The object of the present invention is to create a method which will resolve, amongst other things, the problem outlined above, and the method may accordingly be regarded as being essentially characterized in that, in conjunction with the performance in a treatment unit of one or more first treatment stages for the construction of the bridge, identification data introduced or utilized in the one or more first treatment stages relating to the individual different heights of the anchorage elements above the dentine or a plane passing through same, and different relative inclinations and the positions and directions of the modular elements in relation to one another and to the anchorage elements are obtained and stored, and in that a processing unit which performs a subsequent processing stage is controlled depending on the data thus obtained and stored, so that any bridge elements present in the bridge between the attachment components of the bridge in the anchorage elements are assured a connection via contact surfaces, and directions and dimensions between the attachment components are essentially in line with the direction of the dentine in the sense of its height and width, at the same time with the necessary strength and location within the dental structure.

In a further development of the idea of the invention use is made in the manufacturing process of a working model which constitutes an internal impression of the jaw. The working model is secured to a component which forms part of the treatment unit and is so arranged as to be capable of displacement and/or rotation in its own plane. Contact surfaces between two first modular elements situated adjacent to one another in the bridge are produced in a first displaced and/or rotated angular position of the part, and so on. Data relating to the first and second displaced and/or rotated angular positions of the part are recorded and utilized in a joining machine, for example a welding machine (laser welding machine), forming the processing unit, for the purpose of joining together modular elements at the produced contact surfaces.

The aforementioned processing device can be so arranged for this purpose that it is controlled for the purpose of interacting with a first modular element secured temporarily to a selected anchorage element in same, for the purpose of producing the contact surface on the first modular element. The first modular element is removed once its contact surface has been produced, and a second modular element, which is to be situated adjacent to the first modular element in the bridge, is fitted to the working model on an adjacent anchorage element. The processing device is guided for this purpose into interaction with the second modular element for the purpose of producing its contact surface, which is to make contact with the aforementioned contact surface on the first modular element. This process stage is performed on the other modular elements until all the contact surfaces have been produced, whereupon all the modular elements are attached to the working model.

An arrangement for the execution of the method indicated in the foregoing is characterized essentially in that it comprises, amongst other things, treatment and processing units, whereby identification data introduced or utilized in the treatment unit relating to the individual different heights of the anchorage elements above the dentine or a plane passing through same, and different relative inclinations and the positions and directions of the modular elements in relation to one another are capable of being determined and stored. A further characteristic is that the processing unit is capable of being controlled, by the use of the established identification data, for the purpose of performing its processing of the modular elements in order to achieve a bridge structure in which the bridge elements of the bridge extend between the attachment elements of the bridge and are so dimensioned that the bridge elements are essentially in line with the direction of the dentine and comply with the necessary strength and location requirements within the dental structure.

A further development of the new arrangement involves, amongst other things, the treatment unit exhibiting a part with a mounting surface for the attachment of a working model which constitutes an internal impression of the jaw with the appropriate dummies representing implanted anchorage elements. The aforementioned part is in this case capable of displacement and/or rotation in the plane of the mounting surface and possibly in the sense of the height of the mounting surface. The treatment unit in this case also exhibits a processing device for producing the contact surfaces on the modular units when these are applied one by one to the working model. The treatment device is also arranged for the purpose of determining the displacement and/or angles of rotation at which the different modular elements are processed.

The processing unit is so arranged in the latter case as to perform the joining operation (e.g. laser welding) depending on the data relating to the aforementioned displacements and/or rotations. A conventional cutting wheel can be used for the purpose of producing the contact surfaces. The cutting wheel can be so arranged in this case as to be capable of lateral displacement in order to compensate for the thickness of the wheel. Compensation can be effected alternatively or in a supplementary fashion by the lateral displacement of the part which is capable of lateral displacement.

In a further embodiment the arrangement can contain simulating devices for the simulation of the form of the bridge and the form and positions of the contact surfaces. The processing device in this case utilizes data from the simulation devices as the aforementioned identification data.

Achieved through what is proposed above are a method and an arrangement which permit the economical manufacture of individual bridge structures with the necessary accuracy and strength. The method and arrangement are suitable for bridge structures in titanium.

The embodiments of the method and arrangement in accordance with the invention proposed here are described below with reference to the accompanying drawing, in which.

The designation 1 is used in the Figure in respect of a working model. The working model is produced in a previously disclosed manner and constitutes an impression or moulding of the dentine 2 together with surrounding parts of the person who is to use the artificial dental structure. The working model includes dummies 3b, in accordance with FIG. 2, attached to pins which are implanted in a previously disclosed manner in the person's jaw. Attached to the dummies are spacers 4, the design and application of which are also previously disclosed.

Figure 2:
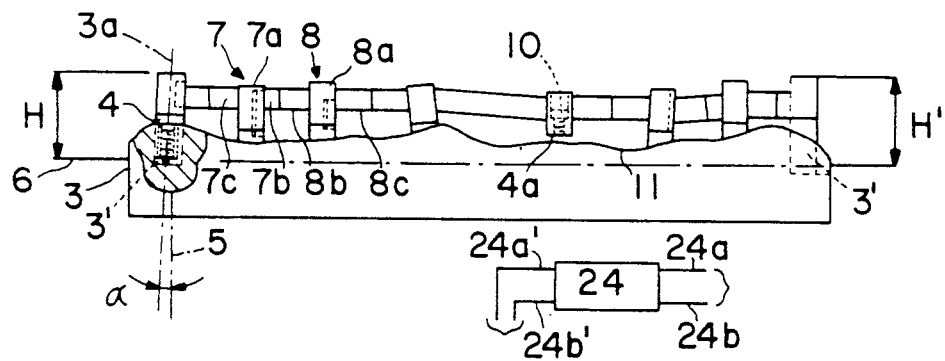
FIG. 2 shows the working model in accordance with FIG. 1 in vertical section.
Figure 3:
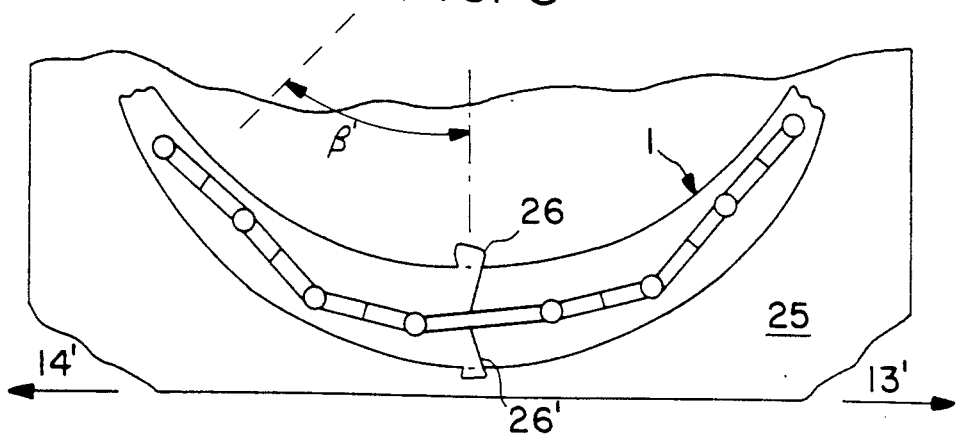
FIG. 3 shows the working model applied to an attachment surface on a processing unit illustrated in section and in principle.

A characteristic feature of the implanted pins is that they adopt individual positions in the dentine, which means that the distance devices project upwards above the dentine to different heights and at different angles of inclination. This is illustrated in FIG. 2 by the external pins 3′ and 3″ having different heights H and H′. In addition the pin 3′ is also inclined in relation to the vertical axis 5 in the actual section in accordance with FIG. 2. The angle between the axis 3a of the pin and the aforementioned vertical axis is indicated by $\alpha$. The pin 3″ exhibits the inclination 0° in the illustrative embodiment shown here. The pin can also be inclined in the other direction, for example perpendicularly to the plane of the paper in accordance with FIG. 2.

The distances H and H′ are indicated respectively with their starting points on a plane 6 which extends perpendicularly to the figure plane in FIG. 2 and through the working model. The different heights H, H′ are dependent on the appearance of the individual dentine, and any inclinations of the implanted pins are dependent on the fact that it is not possible to predict the directions of the pins inserted by an operation.

Figure 1:
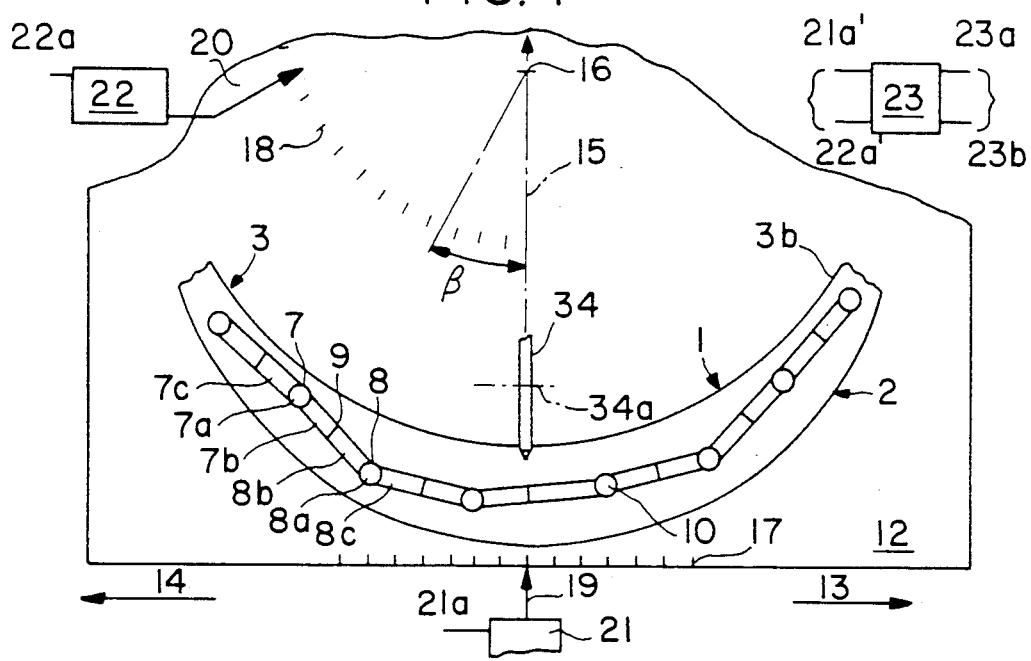
FIG. 1 shows in horizontal view and in principle parts of a working model of an internal impression of a jaw, in conjunction with which the working model has been applied to a mounting surface on a treatment unit used for this purpose.

The bridge framework, which is made of titanium or some other hard material, is built up of modular elements, two of which are indicated by 7 and 8 in FIGS. 1 and 2. These designs of the modular elements can vary within wide limits. Modular elements have been chosen in the present case which exhibit attachment components 7a and 8a with projecting components 7b, 7c and 8b, 8c arranged therein. In conjunction with the construction of the bridge the modular elements are tested in respect of their fit one with the other with regard to the production of the contact surfaces 9. The aforementioned contact surfaces may be situated on the projecting components illustrated in the Figures. Contact surfaces may also be provided, however, on the attachment component 7a and 8a, in which case the projecting component on an adjacent element extends all the way to the central component concerned.

The respective spacers 4 are screwed securely to the respective pins 3 with the help of a screw 4a. This anchorage is previously disclosed and is not affected by the invention, except in the event of the bridge structure being required to be capable of being attached/screwed securely to the spacers 4. In order to achieve this, the screw 4a is provided with a threaded hole for the screw 10. The aforementioned screw 10 extends from the upper surface of the respective attachment component, and the attachment component is provided with an internal shoulder to permit attachment with the help of the screw 10.

In one embodiment the modular elements can contain attachment units 7a and 8a which are capable of displacement in relation to the projecting components 7b, 7c And 8b, 8c. A certain level equalization effect can be achieved in this way with the help of the individual displacement of the attachment component of the modular element in relation to the projecting parts. The modular elements can thus be given a uniform design where the projecting parts originate at the same angle (e.g. a right-angle) from the attachment component. It is possible, however, to cause the projecting parts to originate from their respective attachment components at different angles, so that individual matching in the sense of the height of the jawbone can take place. Each of the modular elements can be provided with one or more projecting parts in relation to the attachment component. What is important is that the projecting parts and the attachment components in the bridge structure are given a flexible form, at the same time as the strength requirements are satisfied. In addition the bridge components should exhibit a clearance to the upper surface of the dentine. The requirement is thus that the bridge elements must essentially make contact with the upper surface 11 of the dentine. The expression 'essentially' shall be interpreted with a broad meaning in this instance, and the level equalization effect achieved by means of the capacity of the attachment components for displacement relative to the projecting parts shall be ignored. It is also essential for the bridge structure to be capable of being formed with comparatively narrow dimensions, so that it is accommodated within the artificial dental structure, which is not shown in the Figures. The requirement imposed on the bridge structure is thus that the bridge elements shall be essentially in line with the direction of the dentine, including in the sense of the width or depth of the dentine.

The treatment device 12 is also provided with a cutting wheel illustrated symbolically by 34. The suspension of the part 12 and the cutting wheel 34 and the driving of the latter can be executed in a previously disclosed manner. The wheel rotates about its own axis 34a. The contact surfaces 9 between the modular elements are produced with the help of the part 12 and the wheel 34. The operation proceeds in such a way that a first modular element, for example the modular element 7, is clamped temporarily in position, whereupon the part 12 is displaced and/or rotated around axis 16 through an angle so that the predetermined cutting point on the projecting part 7b on the modular element is brought into line with the cutting wheel 34. With the help of the latter the projecting part 7b is cut at the predetermined point. The modular element 7 is then loosened and rotated or removed and the cutting wheel is applied to the modular element 8, the projecting part 8b of which is cut with the part 12 in the same position of displacement and/or angular rotation, with compensation for the thickness 21 of the disc. The set position of displacement and/or angular rotation can be sensed with sensing devices 19, 21 and 20, 22. The aforementioned sensing devices exhibit outputs 21a and 22a which are fed into the inputs 21a' and 22a' of a storage unit 23, which is capable of establishing and storing the various adjustment positions for the part 12 in conjunction with the production of the different contact surfaces 9 of the modular elements. The aforementioned data can be obtained at outputs 23a and 23b. These data can be fed into a control unit 24 for a processing unit 25, which in this instance consists of a laser welding machine, an adhesive bonding machine or a joining machine of some other kind. The control unit receives the data from the sensing and storage unit 23 via its inputs 24a and 24b. Control signals are obtained at the outputs 24a' and 24b' of the control unit. The joining machine 25 is controlled in a previously disclosed manner via these control outputs into the different positions which represent the contact surfaces on the modular elements. The working model 1 is clamped to a part on the machine 25 which is able to move in a corresponding manner to the part 12 in the treatment machine. The part in question is thus capable of displacement in the directions of the arrows 13, 13 and 14, 14', that is to say the x-coordinate, and capable of rotation through the angle of rotation $\beta'$. On the event of the part 12 moving in some other manner, for example in the y- and z- coordinates 15, the part 25 will possess equivalent mobility. The joining function for the processing component is symbolized by a pair of welding electrodes 26, 26'. These welding electrodes are given a fixed position, and the part 25 causes the contact surfaces to rotate forwards to the electrodes 26, 26' depending on the control instructions given by the control unit 24.

Figure 4:
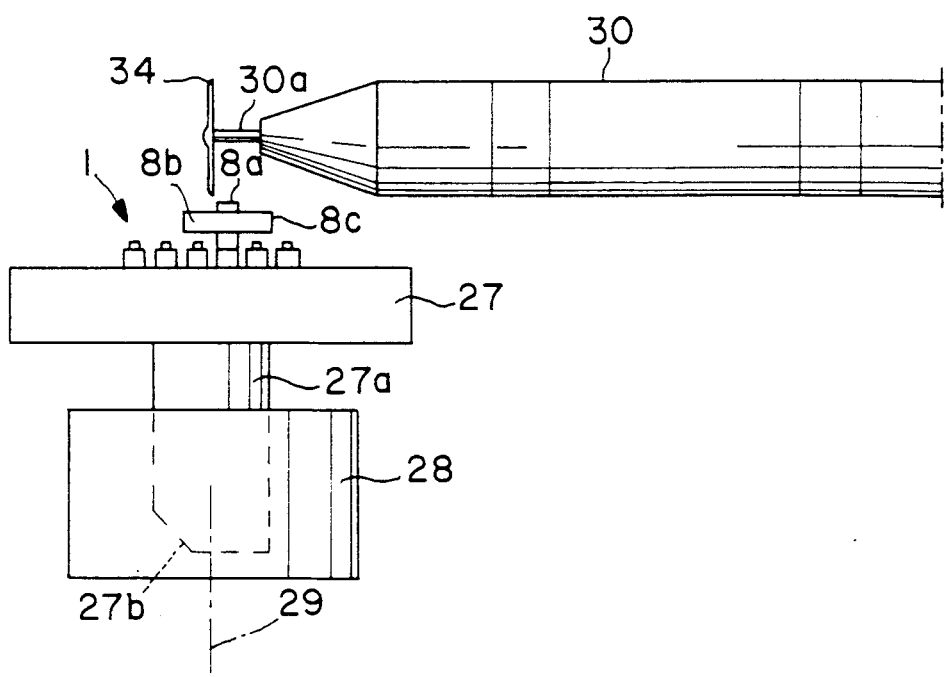
FIG. 4 shows a model holder held in first chuck devices in a first processing station.
Figure 5:
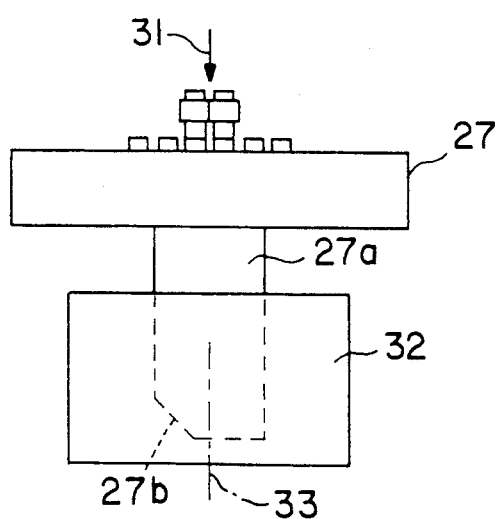
FIG. 5 shows the model holder held in chuck devices in a second processing station.

FIGS. 4 and 5 illustrate an arrangement which is suitable in the event of the processing stations being geographically separated, so that the working model 1 must be moved or transported. The working model is fixed in a previously disclosed manner to a holder 27 arranged with securing devices 27a for its temporary attachment to a first chuck device 28 of a previously disclosed kind. The chuck device is a part of rotating devices (not shown) so arranged as to be capable of causing the chuck device to rotate about an axis of rotation 29 33 for the purpose of adjusting the elements 8b/8c in relation to the cutting device 34. The latter device is arranged on a rotating device 30, via the shaft 30a of the latter. The rotating device can be driven electrically, pneumatically or hydraulically, etc.

The holder 27 is arranged for torsional attachment to the chuck device 28. The aforementioned attachment is achieved by means of a searching device comprising an inclined surface 27b and a heel, etc. The holder is imparted by means of the searching device with a predetermined angular rotational position in the chuck device. 28, which in turn is adjustable in a starting position with the help of a scale 17, 18, heel or similar device.

At the processing station in accordance with FIG. 4 cutting is executed in the manner described above, whereupon transfer can take place to the station in accordance with FIG. 5, where welding is performed at the contact surfaces. A welded joint is indicated by 31. In FIG. 5 the holder is secured in a second chuck device 32 corresponding to the first chuck device. Torsional attachment to and rotation with the second chuck device take place in a similar manner, which means that the joining surfaces are capable of displacement into working positions which correspond to one another in the two instances. The devices which perform the cutting and welding functions can be caused to work in positions which correspond to one another, past which the contact surfaces are caused to move with the help of data transferred from the first station to the second in respect of the rotational positions of the first and second chuck devices.

The data for the identification of the contact surfaces can be executed in a different manner, just as other functions described in the foregoing. The bridge structure and its joining of the modular elements can thus be simulated with the help of previously disclosed simulation devices, for example computer equipment. Construction and joining are calculated from the three-dimensional assumptions which relate to the construction and attachment of the bridge structure. With the help of the data thus obtained, the modular units are each processed individually and are combined into a combination station.

The invention is not restricted to the embodiment referred to above as an example, but may be subjected to modifications within the scope of the following Patent Claims or the idea of invention.

I claim:

1. A method for producing by mechanical means a bridge made of titanium modules for anchorage elements implanted in the dentine of teeth with an artifical dental structure and through which the artificial dental structure is attached to the anchorage elements, the bridge being built up of modular elements which are adapted to interfit with each other and are treated for joining together, said method comprising:
    (a) treating said modular elements in a treatment unit in at least one treatment stage to form contact surfaces between said modular elements;
    (b) obtaining and storing identification data relating to the individual different heights of the anchorage elements above the dentine or a plane passing through said dentine, and different relative inclinations and the positions and directions of the modular elements in relation to one another and to the anchorage elements; and (c) treating the resulting modular elements in a processing unit and controlling the treatment depending on the data thus obtained and stored, so that any bridge elements present in the bridge between attachment components of the bridge and the anchorage elements are assured a connection through the contact surfaces, and directions and dimensions between the attachment components are such that the bridge elements, disregarding any equalization of levels by means of the attachment components, are essentially in line with the direction of the dentine in the sense of its height and width, at the same time having the necessary strength and location within the dental structure.

2. The method according to claim 1, wherein a working model, which constitutes an internal impression of the jaw, is secured to a component which forms part of the treatment unit and is capable of displacement and/or rotation in its own plane; wherein contact surfaces between two first modular elements situated adjacent to one another in the bridge are produced in a first displaced and/or rotated angular position of the component; wherein the contact surface between other modular elements situated adjacent to one another in the bridge is produced in a second displaced and/or rotated angular position of the component, and wherein data relating to the first and second displaced and/or rotated angular positions of the component are recorded and utilized in a joining machine, forming the processing unit, for the purpose of joining together modular elements at the produced contact surfaces.

3. The method according to claim 2, wherein a processing device arranged on the part of the treatment unit, is controlled for interacting with a first modular element secured temporarily to the working model through a selected anchorage element in the model, for producing the contact surface on the first modular element, wherein the first modular element is removed and a second modular element, which is to be adjacent to the first modular element in the bridge, is secured temporarily to an anchorage element adjacent to the anchorage element in the working model, and wherein the processing device is controlled for interacting with the second modular element for producing the contact surface on the second modular element, until all the contact surfaces have been produced, whereupon all the modular elements are attached to the working model and this is transferred to the processing unit onto a part corresponding to the part in the treatment unit.

4. A method according to claim 2, wherein the form and contact surface of the bridge are simulated, and simulation data are utilized as identification data in conjunction with the control of the treatment unit.

5. The method according to claim 1, wherein a processing device arranged on the component of the treatment unit, is controlled for the purpose of interacting with a first modular element secured temporarily to a working model through a selected anchorage element in the model, for the purpose of producing the contact surface on a first modular element; wherein the first modular element is removed and a second modular element, which is to be adjacent to the first modular element in the bridge, is secured temporarily to an anchorage element adjacent to the anchorage element in the working model, and wherein the processing device is controlled for the purpose of interacting with the second modular element for producing the contact surface on the second modular element, and so on, until all the contact surfaces have been produced, whereupon all the modular elements are attached to the working model and the resulting working model is transferred to the processing unit onto a part corresponding to the component in the treatment unit.

6. The method according to claim 1, wherein the form and contact surface of the bridge are simulated, and simulation data are utilized as identification data in conjunction with the control of the treatment unit.

7. An arrangement for producing by mechanical means a bridge made of titanium for anchorage elements implanted in the dentine of a tooth, which bridge constitutes the framework for an artificial dental structure and through which the dental structure is attached to the anchorage elements, for which purpose the bridge is built up of modular elements which are adapted to interfit with each other and are treated for joining together, comprising a treatment unit for obtaining and storing identification data relating to the individual different heights of the anchorage elements above the dentine or a plane passing through said dentine, and different relative inclinations and the positions and directions of the modular elements in relation to one another and a processing unit for utilizing said identification data and for processing the modular elements in order to achieve a bridge structure in which bridge elements extend between attachment elements of the bridge and are dimensioned in such a way that the bridge elements are essentially in line with the direction of the dentine and comply with the necessary strength and location requirements within the dental structure.

8. The arrangement according to claim 7, wherein the treatment unit comprises an attachment surface for securing a working model which constitutes an internal impression of the jaw with dummies representing implanted elements said attachment surface being capable of being displaced and/or rotated in the plane of the attachment surface to various angular positions and a processing device for producing mating surfaces on modular units when these are applied one by one to the working model, said treatment unit being arranged for determining displacements and/or angles of rotation at which the different modular elements are treated.

9. Arrangement according to claim 8, wherein the processing unit is adapted to perform joining of the bridge elements of adjacent modular elements depending on the data relating to longitudinal displacements and/or angular rotations.

10. Arrangement according to claim 9, wherein the processing device contains a cutting wheel capable of interacting with the modular elements in the various displaced and/or rotated angular positions, said wheel being arranged perpendicularly to the attachment surface of the working model.

11. Arrangement according to claim 9, containing simulating devices for the simulation of the form of the bridge and the positions of the mating surfaces, wherein the processing device utilizes the data from the simulation devices as said identification data.

12. Arrangement according to claim 8, wherein the processing device contains a cutting wheel for interacting with the modular elements in the various displaced and/or rotated angular positions, said wheel being arranged perpendicularly to the attachment surface of the working model.

13. Arrangement according to claim 8, containing simulating devices for the simulation of the form of the bridge and the positions of the mating surfaces, wherein the processing device utilizes the data from the simulation devices as said identification data.

14. Arrangement according to claim 7, wherein the processing unit contains a cutting wheel for interacting with the modular elements in the various displaced and/or rotated angular positions, said wheel being arranged perpendicularly to the attachment surface of a working model.

15. Arrangement according to claim 14, containing simulating devices for the simulation of the form of the bridge and the positions of the mating surfaces, wherein the processing device utilizes the data from the simulation devices as said identification data.

16. Arrangement according to claim 7, wherein it contains simulating devices for the simulation of the form of the bridge and the positions of the mating surfaces, and wherein the processing unit utilizes the data from the simulation devices as the identification data.

* * * * *